United States Patent [19]
Provost et al.

[11] Patent Number: 5,728,386
[45] Date of Patent: Mar. 17, 1998

[54] THERMOSTABLE VARICELLA ZOSTER VIRUS

[75] Inventors: Philip J. Provost, Lansdale; Cathy Warren Wadsworth, North Wales, both of Pa.

[73] Assignee: Merck & Co., Inc., Rahway, N.J.

[21] Appl. No.: 652,483

[22] PCT Filed: Dec. 19, 1994

[86] PCT No.: PCT/US94/14722

§ 371 Date: May 22, 1996

§ 102(e) Date: May 22, 1996

[87] PCT Pub. No.: WO95/17503

PCT Pub. Date: Jun. 29, 1995

Related U.S. Application Data

[63] Continuation of Ser. No. 171,048, Dec. 21, 1993, abandoned.

[51] Int. Cl.$^6$ .............................. A61K 39/25; C12N 7/04; C12N 7/08; C12N 7/02
[52] U.S. Cl. .................... 424/230.1; 424/93.6; 435/236; 435/237; 435/239; 435/948
[58] Field of Search ........................... 424/232.1, 230.1, 424/204.1, 184.1, 93.6; 435/240.1, 240.21, 235.1, 236, 237, 239, 948

[56] References Cited

U.S. PATENT DOCUMENTS

| | | | |
|---|---|---|---|
| 3,911,108 | 10/1975 | Singh | 424/172.3 |
| 3,961,046 | 6/1976 | Cerini | 424/212.1 |
| 4,000,256 | 12/1976 | Hilleman et al. | 424/230.1 |
| 4,071,618 | 1/1978 | Konobe et al. | 424/209.1 |
| 4,072,565 | 2/1978 | Weiss et al. | 435/172.3 |
| 4,147,772 | 4/1979 | McAleer et al. | 424/202.1 |
| 4,273,762 | 6/1981 | McAleer et al. | 424/212.1 |
| 4,324,861 | 4/1982 | Kan | 435/237 |
| 4,337,242 | 6/1982 | Markus et al. | 424/202.1 |
| 4,338,335 | 7/1982 | McAleer et al. | 514/777 |
| 4,500,512 | 2/1985 | Barme et al. | 424/218.1 |
| 4,686,101 | 8/1987 | Ellis et al. | 424/186.1 |
| 4,769,239 | 9/1988 | Ellis et al. | 424/186.1 |
| 4,812,559 | 3/1989 | Ellis et al. | 536/23.72 |
| 4,952,674 | 8/1990 | Keller et al. | 530/326 |
| 4,985,244 | 1/1991 | Makino et al. | 424/202.1 |
| 5,006,335 | 4/1991 | Gluck et al. | 424/212.1 |
| 5,024,836 | 6/1991 | McAleer et al. | 424/202.1 |
| 5,075,110 | 12/1991 | Francon et al. | 414/202.1 |

FOREIGN PATENT DOCUMENTS

| | | |
|---|---|---|
| 0 211 756 | 2/1987 | European Pat. Off. . |
| 0 251 534 | 1/1988 | European Pat. Off. . |
| 0 252 059 | 1/1988 | European Pat. Off. . |

OTHER PUBLICATIONS

Davison, et al., "New Common Nomenclature for Glycoprotein Genes of Varicella Zoster Virus . . . ", J. of Virology., vol. 57, No. 3, pp. 1195–1197 (Mar. 1986).

Gershon, et al., "Live Attenuated Varicella–Zoster Vaccine", Reviews of Infectious Diseases, vol. 2, No. 3, pp. 393–407 (1980).

Michalski, et al., "Thermal Inactivation of Rabies and Other Rhabdoviruses: Stabilization by the Chelating Agent Ethylenediaminetetraacetic Acid . . . ", Infection and Immunity, vol. 14, No. 1, pp. 135–143 (1976).

Arbeter, et al., "Combination Measles, Mumps, Rubella, and Varicella Vaccine", Am. Acad. of Pediatrics, pp. 742–747 (1986).

Bennett, et al., "The Effects of Freeze–Drying on the Potency and Stability of Live Varicella Virus Vaccine", Develop. Biol. Standard, vol. 74, pp. 215–221 (Karger, Basel, 1992).

Provost, et al., "Antibody assays suitable for assessing immune responses to live varicella vaccine", Vaccine, vol. 9, pp. 111–116 (Feb. 91).

Takahashi, et al., "Attenuation and laboratory markers of the Oka–strain varicalla–zoster virus", Postgraduate Medical Journal, vol. 61 (Suppl. 4) pp. 37–46 (1985).

Popa & Repanvici, "Enhancement and Stabilization Effect of EDTA on Sendai Virus Neuraminidase Activity", ACTA Biol. vol. 21, pp. 280–287 (1977).

McAleer, et al., "Stability on Storage at Various Temperatures of Live Measles, Mumps and Rubella Virus Vaccines in New Stabilizer*", J. Biol. Stand., vol. 8, pp. 281–287 (1980).

Mariner, er al., "Comparison of the Effect of Various Chemical Stabilizers and Lyophilization Cycles on the Thermostability . . . ", Vet. Microbiol., vol. 21, pp. 195–209 (1990).

Majer, et al., "Freeze–Drying of a Purified Human Diploid Cell Rabies Vaccine", vol. 36, pp. 285–289 (1976).

Languet, et al., "Freeze–Dried Vaccine Against Rinderpest: Stability and Activity Study", Comp. Immun. Microbiol. Infect. Dis., vol. 8, pp. 285–295 (1986).

Howell & Miller, "Effect of Sucrose Phosphate and Sorbitol on Infectivity of Enveloped Viruses During Storage", J. Clin. Microbiol., vol. 18, pp. 658–662 (1983).

Hondo, et al, "Lyophilization of Varicella Virus", Arch. Ges. Virus, vol. 40, pp. 297–299 (1973).

Grose, et al., "Cryopreservation of Varicella–Zoster Virions without Loss of Structural Integrity of Infectivity", Intervirol., vol. 15, pp. 154–160 (1981).

Lopes, et al., "Studies on Yellow Fever Vaccine II—Stability of the Reconstituted Product", J. Biol. Stand., vol. 16, pp. 71–76 (1988).

(List continued on next page.)

*Primary Examiner*—Marian C. Knode
*Assistant Examiner*—Donna C. Wortman
*Attorney, Agent, or Firm*—Joseph A. Coppola; Jack L. Tribble

[57] ABSTRACT

A thermostable varicella zoster virus (tVZV) is useful for the preparation of a vaccine against chickenpox. The tVZV was selected from a population of virus which survived stringent heat inactivation conditions. The surviving virus is used to provide seed virus to produce a new vaccine with enhanced stability.

13 Claims, 1 Drawing Sheet

OTHER PUBLICATIONS

Colinet, et al., "Behaviour of Five Commercial Measles Vaccines in an Accelerated Stability Test", J. Biol. Standardization, Vo. 10, No. 3, pp. 241–247 (1982).

Finter, et al., "Effects of Adverse Storage on Live Virus Vaccines", Dev. Biol. Stand., vol. 41 pp. 271–276 (1978).

Woese, et al., "Thermal Inactivation of Animal Viruses", Ann. New York Acad. Sci., vol. 84, pp. 741–751 (1960).

Allison, et al., "An Accelerated Stability Test Procedure for Lyophilized Measles Vaccines", J. Biol. Stand., vol. 9, No. 2, pp. 185–194 (1981).

THERMOSTABLE VARICELLA ZOSTER VIRUS

CROSS-RELATED TO OTHER APPLICATIONS

This application is a 371 of PCT/US94/14722, filed Dec. 19, 1994, which is a continuation of U.S. application Ser. No. 08/171,048, filed Dec. 21, 1993, abandoned.

BACKGROUND OF THE INVENTION

This invention is concerned with the provision of a thermostable varicella virus for vaccine production. Varicella zoster virus (VZV) causes chicken-pox and zoster (shingles). Chickenpox is a highly contagious disease that occurs in persons with no VZV immunity. More than 90% of the population is exposed during the first two decades of life. The disease is a severe threat to the immunosuppressed and to adults. In many cases, VZV becomes latent in dorsal root ganglion cells. Shingles, a painful chronic condition, occurs when VZV is reactivated from the latent state.

Prevention of chickenpox by vaccination is a desirable goal, and the institution of universal childhood vaccination with a live attenuated varicella vaccine is envisioned. The prior art has reported the propagation of VZV in various cell culture systems and the use of live, attenuated, cell-free VZV as a vaccine. U.S. Pat. No. 3,985,615 describes the production in guinea pig primary embryonic cells of attenuated varicella virus. Virus produced according to that process, the Oka strain of VZV, is suitable for vaccine use and has been deposited with the ATCC as VR-795, although other strains of varicella may be used to produce attenuated VZV according to the U.S. Pat. No. 3,985,615 and other known processes (see U.S. Pat. Nos. 5,024,836; and 4,000,256). U.S. Pat. No. 4,008,317 describes the cultivation of a temperature-sensitive mutant of VZV in WI-38 cells. Compositions useful for the maintenance of viable VZV, such as SPGA, are also known in the art, (see U.S. Pat. Nos. 4,147,772; 4,000,256; 4,337,242, and 4,338,335).

VZV is a member of the herpesvirus family. VZV has been isolated and provided as a live attenuated virus vaccine which is effective to prevent varicella infection in children (U.S. Pat. Nos. 3,985,615; 4,000,256; 5,024,836). No effective, inactivated VZV vaccine has been developed, and VZV rapidly loses viability at ambient temperatures. Thus, a constant problem with VZV vaccines of the past has been the need to store the virus at temperatures below freezing point. This has typically meant that the live attenuated vaccine, even when lyophilized, must be stored in a stabilizing medium at reduced temperatures, such as −15° C. or −20° C. Under these conditions, the live attenuated vaccine viability half-life is approximately 36 months. At −70° C., the haft life is much longer (on the order of many years). However, where the live attenuated vaccine must be stored at higher temperatures, such as at 4° C. or higher, as in third world countries where refrigeration of vaccines at any temperature is difficult, the virus viability drops off very rapidly. Thus, there has been a need for a more stable live attenuated VZV vaccine. This invention meets that need.

SUMMARY OF THE INVENTION

A thermostable live attenuated varicella zoster virus (tVZV) is produced by selection and growth of virus which survives heat inactivation. It was not predictable that heat stable VZV would be produced. The tVZV is useful to produce a new live attenuated varicella zoster virus vaccine with innately increased thermostability.

DETAILED DESCRIPTION OF THE INVENTION

Figure 1:
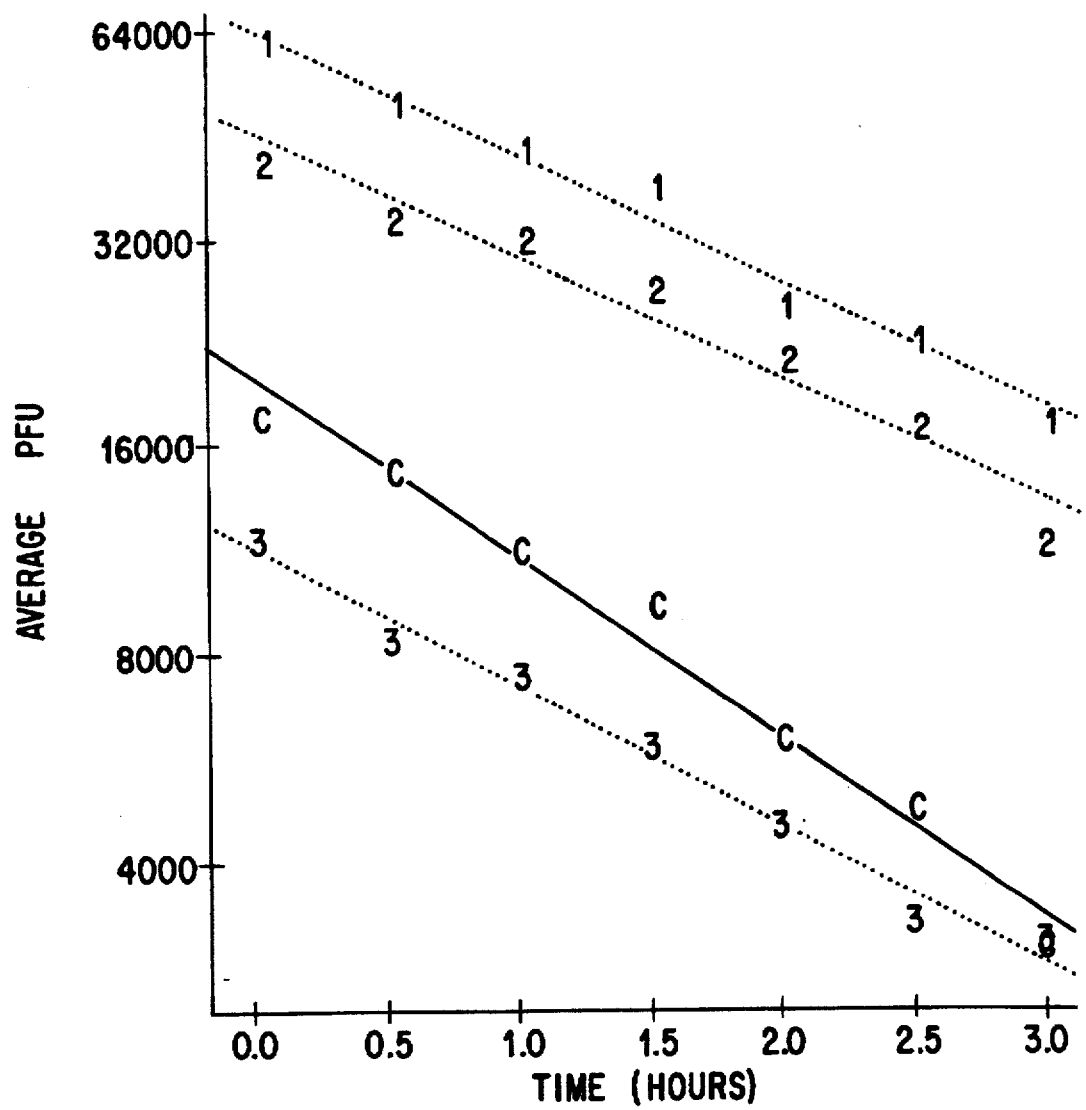
FIG. 1: Linear regression curve showing thermostability of the new tVZV of this invention at 35° C.

Varicella zoster virus (VZV) can be isolated from the papular eruptions of children in the acute phase of chickenpox. VZV isolated in this manner is cultured in vitro over multiple passages to produce a live, attenuated virus. This can be accomplished according to U.S. Pat. No. 3,985,615, hereby incorporated by reference.

According to one embodiment of the instant invention, a live attenuated VZV vaccine is lyophilized after culture and attenuation according to methods known in the art. The lyophilized virus is then subjected to an extended period, about 5–19 days, at an elevated temperature, 25°–75° C. Following the inactivation cycle, residual viable virus is recovered and selected in tissue culture. The virus selected in this manner is then propagated and formulated, either in a liquid or lyophilized state, according to methods known in the art, and is provided as a live attenuated VZV vaccine of improved thermostability, referred to hereinafter as tVZV.

The utility of attenuated, cell-free VZV as a vaccine to prevent chickenpox has been demonstrated. Multiple clinical studies have conclusively proven this utility, and such proof is now part of the prior art [see for example, *Pediatrics*, 88 (3), 604–607 (1991); *Pediatrics*, 87, (5), 604–610 (1991)]. Thus, the tremendous contribution that this invention makes to the art is that it provides a thermostable VZV, tVZV, making ready availability of the virus for stable vaccine formulation more feasible. It was not predictable that a heat stable VZV would be isolated.

tVZV prepared according to this invention may be formulated as a vaccine according to methods known in the art, and administered according to regimens by now well established. For example, the live, attenuated, cell-free tVZV product of this invention may be diluted into stabilizer, filled in bottles, lyophilized in unit doses such that upon storage at about 4° C. or lower, and preferably at about −20° C., a dose of about 1000 PFU will be available at the time of use. The VZV vaccine produced according to the process of this invention may be used in unit dose formulations to inoculate humans to induce immune-responses protective against infection by virulent strains of VZV. Preferably, at a minimum, a dose of about 2000 PFU/ml (1000 PFU/0.5 mL dose) is administered subcutaneously or intramuscularly. Doses of attenuated VZV as high as a total of 15,000 to 20,000 PFU have been administered and are acceptable.

The tVZV of this invention is useful to prepare a thermostable live attenuated VZV vaccine. It is also useful to prepare an immunogen to boost immune responses to VZV in seropositive individuals. The tVZV is also useful as a tool to analyze genomic changes responsible in conferring increased thermostability to viruses. Accordingly, the tVZV genome of this invention is analyzed for restriction fragment length polymorphisms (RFLP's) or the genome is sequenced according to methods well known in the art. In this manner, variations in the genome conferring this enhanced thermostability are identified.

Vaccine formulations of VZV are well known in the art. Thus, according to U.S. Pat. No. 3,985,615, the VZV may be formulated in a sterile, 5% sucrose solution. More complex formulations, such as SPGA (0.218M sucrose, 0.00376M $KH_2PO_4$, 0.0071M $K_2HPO4$, 0.0049M potassium or sodium glutamate, 1% human serum albumin) which further enhance the stability of the VZV are also known in the art. Thus, U.S. Pat. No. 4,000,256 discloses a stabilizer comprising sucrose, albumin, glutamate, and phosphate. Similarly, U.S. Pat. No. 5,024,836 discloses a lyophilized composition comprising VZV and measles, mumps, and rubella in a stabilizer wherein the moisture content is maintained between 2–8% to improve virus stability. These formulations are referred to generically herein as pharmaceutically acceptable carriers and the disclosure of these patents is hereby incorporated by reference.

In addition to the tVZV and a pharmaceutically acceptable carrier, combination vaccines may be prepared incorporating other vaccine entities. Thus, a tetravalent vaccine also including measles, mumps and rubella (M-M-R-V) is contemplated by this invention. Such combinations using attenuated but not thermostable VZV are known in the art [see D'Hondt, EP-A-0 252 059; see also Arbeter, et al., Pediatrics, 76(suppl.):742–747 (1986)]. tVZV could likewise be combined with known DTP vaccines, influenza, hepatitis B, hepatitis A, Haemophilus influenzae b polysaccharide vaccine, Streptococcus pneumoniae polysaccharide vaccines.

These formulations as well as other known methods of formulating and storing VZV are applicable to the production of a vaccine incorporating the tVZV of this invention.

Thus, this invention provides, in one embodiment, a process for preparing a live attenuated thermostable varicella zoster virus (tVZV) having improved stability, which comprises:

a) heating a lyophilized preparation of live attenuated VZV under highly inactivating conditions; and b) selecting and culturing residual live VZV. As defined herein, "highly inactivating conditions" refers to a heat treatment in which anywhere between 1/100 to 1/1000,000 virus particles in a given preparation survive in a viable state. Preferably, an inactivation with a survival rate of about 1/1500 is used.

In another embodiment, this invention provides a thermostable varicella zoster virus having a rate of inactivation equal to about 50% per hour at 35° C., as compared with a rate of 79% per hour for untreated VZV under the same conditions. Thus, according to this method, a decrease in the rate of inactivation at 35° C. of about 38% (50/79×100) for a given strain of VZV can be expected based on the instant patent disclosure. In addition, from this invention, it is predictable that at least a proportional increase in half life, from about 36 months to about 60 months, occurs when the virus is stored lyophilized at –15° C. or below. Further enhancements in thermostability are achievable by processing the thermostable VZV of this invention through additional heat inactivation and selection of a yet more thermostable VZV isolate. The 38% enhanced stability of tVZV demonstrated herein at 35° C. is predictably at least proportionally applicable to tVZV stored at reduced temperatures such as 4° C., –20° C., or –40° C. Furthermore, optimization of stabilizing solutions or storage conditions, such as the use of 2–4% moisture in a lyophilized formulation, according to the teaching of U.S. Pat. No. 5,024,836, hereby incorporated by reference, may be applied to further enhance the stability of the tVZV of this invention.

In another embodiment, this invention provides a method of using a tVZV to make an anti-VZV vaccine which comprises providing a minimum of about 1000 plaque forming units of the tVZV in a pharmaceutically acceptable carrier.

Another embodiment is a vaccine comprising the tVZV.

The infectivity titers of varicella zoster virus (VZV) preparations are obtained by an agarose-overlay or liquid overlay procedure described by Krah et al., (J. Virol. Methods, 1990, 27:319–326). Briefly, this method involves culturing MRC-5 cells, which are susceptible to VZV infection, to an actively replicating state, that is, to a point where the cells are about 50–80% confluent. Virus is then overlaid onto the cell monolayer in a minimal volume, allowed to attach to the cells and then additional growth medium is added. After several days of growth, the cells are exposed to a protein stain, and clear areas, plaques, are counted. Thus, for a known volume of viral inoculum, the number of plaque forming traits (PFU) per milliliter represents a good measure of virus yield. Multiplied by the total volume of cell-free virus obtained from any given viral preparation, the total number of PFU may be calculated.

tVZV prepared according to the method of this invention has been deposited with the ATCC under the Budapest Treaty on Nov. 15, 1993 and accorded deposit numbers of: VR 2437, VR 2438, and VR 2439.

The foregoing description teaches generally how to make the VZV vaccine of this invention having improved thermostability. The following examples are provided to teach more particularly how this invention may be carried out. However, the invention should not be construed as being limited to the specifics of the examples.

EXAMPLE 1

Thermal Inactivation and Recovery of Thermostable VZV

Five hundred intact, unreconstituted vials of Varivax®, lot CR453, obtained from Merck & Co., Inc., were heated at 50° C. for 12 days. All 500 heated vials were placed at –20° C. storage pending analysis. Subsequent analysis gave the following:

1. Residual live virus was titered at 2.4 PFU/ml, while the standard, unheated CR453 vials were titrated at 3830 PFU/ml. Thus, there was a 99.94% reduction in viable VZV under these conditions of thermal inactivation. Thus, a treatment analogous to this is defined herein as "highly inactivating conditions".

2. Total VZV antigen by dot-blot assay was 9.8 units/ml, in the heated vaccine. Standard unheated vaccine tested simultaneously gave 9.4 units/ml. The value at time of original release in 1987 was estimated at 9.5 units/ml.

3. Western Blot: This assay indicated no grossly detectable differences in heated and unheated CR453. Both human zoster serum, (a polyclonal anti-VZV serum), and mouse monoclonal antibody to virus glycoprotein 1 were used.

EXAMPLE 2

Demonstration of Enhanced Stability of Varicella Recovered from Heat Treatment

Four vials of heat inactivated CR453 prepared as described in Example 1, and one vial of normal CR453 were each reconstituted with 0.7 ml sterile distilled water and placed on ice. From each heat inactivated vial, 0.5 ml (estimated 1.2 plaque-forming units) and 0.5 ml from the unheated vial (estimated 1915 plaque forming units) was used to inoculate MRC-5 cells in culture, at 0.1 mL per 60 mm plate, five plates per isolate. The medium used was EMEM containing 2% fetal calf serum plus neomycin and 2 mM Glutamine.

It was anticipated, based on the known titer of 0.24 PFU/0.1 mL, that under the conditions described above, each plate inoculated with heated VZV would receive one or less live VZV plaque forming units.

These samples were taken through 5 passages as summarized in Table 1 below, essentially as follows:

Passage level 1, P1

Prior to inoculation at each level of virus passage, MRC-5 cells were grown in culture to near confluence. For P1, the medium was aspirated from cell culture sets (one set for each VZV isolate) consisting of five 60 mm plates, and each plate was inoculated with 0.1 ml of virus sample per plate. The cultures were incubated at 35° C., 5% $CO_2$ for 1 hr., and fed with 5 mL of medium per plate. After seven days, the plates were scanned microscopically for formation of VZV plaques (cytopathic effects, CPE). P1 plates inoculated with VZV material from heated vials 1–4 showed no detectable CPE. Plates inoculated with normal VZV had 90% CPE, (the uninoculated plate at every passage level had no CPE). Each set of plates was washed with PBS, and the cells were harvested by addition of 0.5 ml trypsin per plate and incubated 5 min. The cells from each grouping of five plates (i.e., five for isolate 1, five for isolate 2 etc.) were removed and pooled. The pooled cells for each isolate were pelleted, and the supernatant was aspirated. Medium (25 mL) was then added to the pelleted cells to form a P1 suspension which was used to inoculate MRC-5 plates to form passage level 2:

Passage level 2, P2

Five 60 mm plate per isolate were each inoculated with 5 mL of P1 cell suspension after aspirating medium from the MRC-5 cells. After 5 days, the plates were scanned microscopically. Plates from heated vials 1–3 each had 1–3 visible plaques. Plates inoculated with heated vial number 4 VZV showed no signs of CPE. The plates inoculated with unheated VZV had 90% CPE. Each set of plates was washed with phosphate buffered saline and then treated with 0.5 mL trypsin. For each set, cells from three plates were pooled, pelleted and resuspended in 6 mL of freezing diluent (EMEM, 15% DMSO, 10% fetal calf serum), aliquoted and stored in liquid nitrogen in 1 mL aliquots. The remaining two plates per set were pooled, pelleted and resuspended in medium (20 mL) to form a P2 suspension which was used to inoculate MRC-5 plates to form passage level 3:

Passage level 3, P3

Four 60 mm plates per isolate were each inoculated with 5 mL of the P2 isolate per plate after aspirating medium from the MRC-5 cells. After three days, the plates were scanned microscopically. Plates from heated vials 1–3 had 40%, 20% and 20% CPE respectively. Plates inoculated with heated vial number 4 VZV showed no signs of CPE. The plates inoculated with unheated VZV had 20% CPE. Each set of plates was washed with phosphate buffered saline and then treated with 0.5 mL trypsin. For each set, all the cells were pooled using 5 mL media per plate, pelleted and resuspended in 6 mL of freezing diluent (EMEM, 15% DMSO, 10% fetal calf serum), aliquoted and stored in liquid nitrogen in 1 mL aliquots, to form the P3 stock used to inoculate cells for P4:

Passage level 4, P4

Two 150 $cm^2$ flasks were each inoculated with 1 mL of thawed P3 isolate (except for isolate 4 which was aborted due to non-appearance of any CPE up to P3). After 3 days flasks inoculated with heated isolates, 1–3 each had 70% CPE. Flasks inoculated with P3 of the unheated VZV isolate had 40% CPE. Each flask was rinsed three times with phosphate buffered saline, aspirated, and the cells harvested by adding 5 mL trypsin to each flask and incubating for 5 minutes at 35° C. Cells from each set of flasks were pelleted and resuspended in 30 mL of medium, to form the P4 stocks used to inoculate cells for P5:

Passage level 5, P5

Sets of six 150 $cm^2$ flasks per set were each inoculated with 5 mL of P4 suspension per flask. After 2 days, isolate 1–3 flasks each had 50–60% CPE while flasks inoculated with normal P4 VZV each had about 40% CPE. Each flask was washed three times with phosphate buffered saline and aspirated. VZV stabilizing solution was added to each flask (7 mL) and the cells recovered by scraping, and then aliquoting 15 mL per 50 mL centrifuge tube. Each tube was then sonicated for 5 minutes followed by centrifugation at 2200 rpm for 10 minutes. The supernatants from each set were pooled and aliquoted in 2.5 mL aliquots and frozen at −70° C.

The foregoing description of virus growth for each isolate and normal CR453 is summarized in Table 1:

TABLE I

ISOLATION AND PROPAGATION OF THERMOSTABLE VZV VARIANTS: # OF PLAQUES PER PLATE (PASSAGE 2) OR % CPE ON PLATE (FOR ALL OTHER PASSAGES):

|  | ISOLATE 1 | ISOLATE 2 | ISOLATE 3 | ISOLATE 4 | NORMAL 453 |
|---|---|---|---|---|---|
| PASSAGE 1 5 × 60 mm plates @ 7 days | 0 | 0 | 0 | 0 | 90 |
| PASSAGE 2 5 × 60 mm plates @ 4 days | 1–3 plaques | 1–3 plaques | 1–3 plaques | 0 | 90 |
| PASSAGE 3 4 × 60 mm plates @ 3 days | 40 | 20 | 20 | 0 | 20 |
| PASSAGE 4 2 × 150 $cm^2$ flasks @ 3 days | 70 | 70 | 70 | * | 40 |
| PASSAGE 5 6 × 150 $cm^2$ flasks @ 2 days | 60 | 60 | 55 | * | 40 |

*Isolate was aborted at passage 3 due to absence of any detectable CPE.

The growth of each heated isolate at each passage level appeared to be similar. Virus stocks produced at Passage 5 for Isolates 1, 2 and 3 along with normal CR453 were harvested and stored as sonicated, cell-free virus at −70° C. Passage 3 of Isolate 4 was aborted because of no apparent cytopathic effect (CPE).

To determine the number of plaque-forming units for each stock, a plaque assay was performed:

| VIRUS STOCK | TITER |
|---|---|
| ISOLATE 1, (tVZV1) | 86,200 pfu/ml |
| ISOLATE 2, (tVZV2) | 69,000 pfu/ml |
| ISOLATE 3, (tVZV3) | 10,840 pfu/ml |
| CONTROL 453 | 35,000 pfu/ml |

For deposit with the ATCC, P5 virus of each tVZV isolate was expanded at passage level 6 and frozen in 1 mL aliquots. tVZV1 was accorded ATCC number VR2437. tVZV2 was accorded ATCC number VR2438. tVZV3 was accorded ATCC number VR 2439.

STABILITY ANALYSIS

For each isolate of virus stock, (tVZV1, tVZV2, tVZV3, and control, unheated CR453) a 1:20 dilution of the P5 material was made in a stabilizing solution at 35° C. and incubated at 35° C. Samples were taken from each diluted isolate at time intervals of 0 hr, 0.5 hr, 1.0 hr, 1.5 hr, 2.0 hr, 2.5 hr, and 3.0 hr. Aliquots were frozen and stored at −70° C.

Samples from each time-point were then tested by plaque assay to determine and compare stability. Six replicate stability assays were performed in this manner to determine the rates of decay for each isolate and the control vaccine. The three tVZV isolates appear to have similar rates of decay (see Table 2 and FIG. 1). An average value of the six stability assays shows there is no significant difference among the isolates (decay rate=50% per hr). However, the control vaccine CR453 decayed at a rate of 79% per hr. In a lyophilized state, control vaccine loses viability at a rate of approximately 28% per day at 30 degrees. For lyophilized tVZV, this rate is predictably slower by approximately 38% (50/79; i.e., only about 17% loss per day). The slopes of each isolate showed a consistently lower rate of decay when compared to the control vaccine for each stability assay.

TABLE 2

VARICELLA ISOLATE STABILITY EXPERIMENT
ESTIMATED FOLD DECREASE IN POTENCY PER HOUR (%)

| RUN | CONTROL | ISOLATE 1 | ISOLATE 2 | ISOLATE 3 |
|---|---|---|---|---|
| 1 | 1.79 (79%) | 1.40 (40%) | 1.34 (34%) | 1.70 (70%) |
| 2 | 1.76 (76%) | 1.43 (43%) | 1.36 (36%) | 1.32 (32%) |
| 3 | 1.44 (44%) | 1.24 (24%) | 1.38 (38%) | 1.28 (28%) |
| 4 | 1.74 (74%) | 1.53 (53%) | 1.51 (51%) | 1.68 (68%) |
| 5 | 1.94 (94%) | 1.52 (52%) | 1.44 (44%) | 1.80 (80%) |
| 6 | 2.18 (118%) | 1.80 (80%) | 1.69 (69%) | 1.58 (58%) |
| Pooled Average | 1.79 (79%) | 1.49 (49%) | 1.46 (46%) 1.50 (50%) | 1.55 (55%) |

Note: There is a statistically significant difference in slopes between the control and heated isolates, while there is no difference among the heated isolates ($P < 0.01$).

EXAMPLE 3

Assay For VZV Yield Determination

The infectivity titers of varicella zoster virus (VZV) preparations were estimated using the agarose-overlay or liquid overlay procedure described by Krah et at., (*J. Virol. Methods*, 1990, 27:319–326). The assay for the liquid overlay and the agarose-overlay method is performed as follows:

MRC-5 cells are seeded in 60-mm tissue culture plates, at $6\times10^5$ cells in 5 mL volumes of BME (Basal Medium Eagle with Hanks'balanced salts solution) with 1000 mg/L galactose, 50 μg/mL neomycin, 2mM L-glutamine, and are incubated at 35° C. in a 5% $CO_2$ atmosphere. After incubation for 24–48 hours, the cells reach 50–80% confluency. The growth medium is removed by aspiration, and cells are infected with 100 μl of VZV solution diluted in appropriate virus diluent, such as SPGA buffer, or liquid maintenance medium (LMM). SPGA buffer contains 7.5% (w/v) sucrose, 11 mM potassium phosphate, 0.1% (w/v) sodium glutamate and 1% human serum albumin. Virus is allowed to attach for >1 hour at 35° C. in a 5% $CO_2$ atmosphere. The VZV-infected cell cultures are then overlaid with 5 mL agarose overlay medium (AOM) or liquid maintenance medium (LMM). Agarose overlay medium is a mixture of two solutions, liquid overlay medium (LOM) and agarose solution. LOM contains minimal essential medium with Earle's salts (MEM), 2% heat-inactivated fetal calf serum, 50 μg/mL neomycin sulfate and 2 mM L-glutamine. Agarose solution is prepared by heating 4.5 g of low gelling temperature agarose in 100 mL MEM for 15 min at 121° C. and allowing the solution to cool to 45° C. AOM is prepared by mixing one volume of agarose solution with 4 volumes of a 1.25× concentrate of LOM at 45° C., (for the liquid overlay method, a 1× concentration of LOM is used and need not be heated or cooled). The plates are cooled to 23–25° C. to permit the AOM to solidify. The cultures are incubated to allow plaque development. After 6–7 days, plates which received AOM are overlaid with 5 mL of phosphate-buffered saline (PBS) and rimmed with a glass Pasteur pipette to loosen and remove the agarose. Medium is aspirated from plates which received LMM. Plaques are visualized by staining cells with a solution of 0.2% (w/v) Coomassie Blue R-250 in ethanol-1% acetic acid. Plaque counts are the average of 4–5 replicate plates and expressed as plaque-forming units per mL (PFU/mL).

EXAMPLE 4

Quantitative Dot-Blot Assay Of Varicella-Zoster

The procedure described herein allows quantitation of VZV antigen. It is accomplished by measuring actual counts per minute of radioactivity in reacted dot-blots rather than using X-ray film. This procedure is intended for estimating total VZV antigen in clarified dispensed VZV vaccine bulk samples.

Materials and Reagents

A. Equipment

1. Polystyrene snap-lock boxes approximately 8"×12"×1½".
2. Rocker platform (Bellco Glass Co., Model 6-044).
3. Nitrocellulose. (ProMega Biotec, 0.45 μl pore size, 15×15 cm).
4. 4° C. Refrigerator or Cold Room.
5. Pipetters 0–100 μl dispensing with disposable tips.
6. Micro Centrifuge Tubes, disposable, polypropylene 1.5 ml capacity.
7. Gamma Counter suitable for counting $^{125}I$.
8. Disposable test tubes for use in Gamma Counter.

B. Reagents

1. Phosphate-buffered saline.
2. Sodium Dodecyl Sulfate (SDS) Bio-Rad Catalog #161-0302.
3. Nonidet NP-40 (Sigma No. N6507).
4. Fetal Calf Serum (FCS).
5. Albumin, Bovine Fraction V (BSA) Calbiochem #12659.
6. Sodium Azide (Sigma).
7. $^{125}I$ Protein A 0.1 mCi/ml (Amersham). To be used within one month date of product.
8. VZV Reference Antigen (VZV Lot 851) stored at −70° C.
9. VZV Positive Antiserum (O.L.I. high-titered zoster serum, labeled HSV143-80 O.I., 8/20/80). Human. 10. Four roller bottles of confluent MRC-5 cells.
11. Whatman 46 cm×57 cm — 3 mm paper (blotting paper) (catalog #3030917).
12. Triton X-100 (TX-100) ('Sigma No. T6878).
13. VZV Negative Control Antigen.

C. Preparation of Reagents

1. Quench Buffer (Q Buffer):
   a. 3L RCM8
   b. 6 gm SDS
   c. 0.6 gm Sodium azide
   d. 70 gm BSA
   e. 30 ml Nonidet NP-40

2. Quench buffer with 1% FCS (blocking buffer)
   a. 50 ml quench buffer+0.5 ml FCS
3. RCM8 with 0.05% Triton X-100
4. Antisera: O.L.I. Human Zoster Serum
   a. dilute 1:2500 in 50 ml Q buffer
5. Sonicate MRC-5 cell extracts: Scrape 4 roller bottles with 5 ml RCMS/bottle, then rinse all 4 bottles with 10 ml RCMS; pool all. Cool to 4° C., sonicate 3 min and bring to 40 cc with RCM8.
6. $^{125}$I Protein A Solution: Dilute 125 μl+50 II Q buffer (0.25 μCi/ml).

Procedure

A. Day 1
1. Prepare sonicated MRC-5 cell extract (cell solution) and place in snap-lock box, along with 2 nitrocellulose sheets [20 cm×40 cm (blocking sheet)].
2. Rock at 4° C. approximately 3 hours.
3. Add 50 ml Quench buffer and rock an additional hour.
4. Make antibody dilution, remove blocking sheets from cell solution and place one blocking sheet in antibody solution. Rock overnight at 4° C.
   NOTE: Step 1 through 4 can be done several days before assay is performed; store blocked antisera at 4° C. (remove blocking sheets and discard sheets after overnight rock in this case).

B. Day 2
5. Add Triton X-100 to 0.05% in undiluted test samples. Draw grid on nitrocellulose sheet to account for all samples (Attachment 111). Dilute reference vaccine (851) and negative control 1:8 in RCM8 containing 0.05% TX-100. Serially dilute 2-fold through 1:64. Test samples are diluted in same manner; however, only 1:16 and 1:32 dilutions are used. Antigens are spotted in duplicate, 5 μl per dilution, on the nitrocellulose grid. Let dry 15 min at room temperature.
6. Place nitrocellulose test sheet in Q buffer with 1% FCS (immerse slowly and evenly) and rock at 4° C. for 1.5 to 18 hours.
7. Remove blocking sheets from antibody solution, place test nitrocellulose sheet into antibody solution and rock overnight at 4° C.

C. Day 3
8. Wash nitrocellulose with Quench buffer on rocker approximately 2 hours, changing buffer every 20 min. Use about 50 ml/wash.
9. Drain and add 50 ml [$^{125}$I] protein A in Q buffer to test sheets and rock 2 hrs on rocker. Dispose of all radioactive materials in appropriate radiation waste containers.
10. Wash test sheet with Q buffer approximately 1.5 hrs, change buffer every 20 min. Dispose of first 4 washes in containers for radiation.
11. Blot test sheet with blotting paper.
12. Cut test sheets according to grid, and place each individual dilution blot into a labelled test tube.
13. Count each tube 1 min using $^{125}$I Gamma Counter.
14. Calculation of Results: A standard antigen has 26 units of VZV antigen per ml. At 1:8, 1:16, 1:32, and 1:64 dilutions, it has 3.25, 1.63, 0.81, and 0.40 traits of antigen per ml. A standard curve is constructed for each run of the assay by plotting mean c.p.m. obtained at each known concentration of antigen. The antigen concentration in the test samples is obtained by finding the antigen level on the Abscissa corresponding to the mean c.p.m. at each test dilution. The final antigen estimate is the mean of the values obtained at each test dilution. Antigen values for undiluted test samples are calculated by appropriate correction of dilution.

MRC-5 antigen is included in each test as a control in the procedure. In practice, only low c.p.m. have been detected in MRC-5 blots and no corrections of test antigen c.p.m. have been made.

EXAMPLE 5

ELISA For Quantitation Of VZV Antigen

A rapid VZV antigen ELISA permits measurement of VZV antigen amounts to permit monitoring of virus growth during manufacture of live varicella vaccine. Additionally, this test can be used to estimate VZV antigen amounts in clarified, sonicated vaccine bulks, and potentially to measure antigen in filled lyophilized vaccine vials. Briefly, this assay is conducted by incubation of VZV antigen from test samples with anti-VZV serum in solution. Remaining free antibody is allowed to bind to VZV antigen mobilized on ELISA microtiter plates. The amount of antibody capable of binding to the plates is inversely proportional to the amount of antigen in the test sample. Antibody binding to the plates is quantitated by reaction with an enzyme-linked anti-human antibody and appropriate substrate to provide a colored product which is quantitated spectrophotometrically.

The VZV antigen ELISA and the VZV plaque assays should generally provide correlative data, but it should be borne in mind that the VZV antigen assay detects non-viable as well as viable VZV. Since the immune response generated by killed VZV has not been shown to be as effective as the response to live attenuated virus, the plaque assay is the critical assay for determination of viral inoculum dose for VZV vaccines. However, the antigen assay is also valuable in that it provides a measure of the total antigen load being administered to a VZV vaccine recipient.

Test Procedure

1. ELISA plates are coated with glycoproteins (gps) from VZV-infected or uninfected MRC-5 cells, and are overcoated with 1% bovine serum albumin [fraction V, #A-9647, Sigma], 0.1% NAN3) to reduce non-specific adsorption of antibodies to the plates. Alternating rows are coated with VZV or control antigen (i.e., rows A, C, E, and G receive VZV gp and rows B, D, F, and H receive uninfected MRC-5 gp antigen).
2. Clarified (3250 g-min) test antigen is diluted in stabilizer in 12×75 mm tubes or microtubes. A standard virus antigen preparation (26 units/mL VZV antigen by dot blot assay) is diluted 1:10 and then serially 1:1.25-fold to provide antigen concentrations of 2.6, 2.1, 1.7, 1.3, 1.1, 0.9 units/mL. Additional dilutions may be included to provide 0.7 and 0.5 units/mL of antigen. This dilution series is used to generate a standard curve for the measurement of antigen amounts in test samples.
3. A human anti-VZV serum is diluted in stabilizer to 2 times the final desired dilution.
4. Three hundred ml volumes of diluted antigen are dispensed into microtubes, mixed with 300 ml diluted anti-VZV serum and incubated at 35° C. for 15–22 min. A control includes human anti-VZV and diluent (no antigen).
5. Aliquots of 100 ml from each serum-antigen mixture are added to 2 replicate VZV glycoprotein (VZV gp) coated wells and 2 MRC-5 gp coated wells (4 wells per sample) (e.g., sample 1 in column 1, rows A, B, C, and D; sample 2 in column 2, rows A, B, C, and D; etc.).

6. Plates are incubated for 15+1 minute at 35° C. to allow free antibody (not complexed to antigen in solution) to bind to virus antigen immobilized on the plates.

7. Unbound antibody is removed by washing and wells receive an alkaline phosphatase conjugated goat anti-human IgG to detect bound human antibody.

8. After incubation for 15+1 minute at 35° C., unbound conjugate is removed by washing. Bound conjugate is detected by incubation for 15 min at 35° C. with p-nitrophenyl phosphate substrate dissolved in diethanolamine buffer.

9. After termination of the substrate reaction by addition of 50 ml/well 3 M NaOH, color development (OD at 405 nm) is quantitated using a microplate spectrophotometer.

1. Test Calculations and Interpretation

Respective replicate OD values for the replicate VZV and MRC-5 coated wells are averaged. Experience has shown the MRC-5 OD to be consistent between different samples and dilutions. Therefore, the MRC-5 values for the entire plate are averaged and used to correct for non-specific binding of the primary antibody or conjugate to uninfected cell extracts. The averaged MRC-5 OD is subtracted from the respective averaged VZV ODs to provide VZV-specific OD ($\Delta$OD) values.

2. Generation of a standard curve for measurement of antigen amounts

The standard curve $\Delta$OD values are plotted against the known antigen concentrations (units VZV/mL). The data are entered into an appropriate graphics program (e.g., Cricket Graph version 1.3, Cricket Software, Malvern, Pa.), the linear portion of the curve is identified (must include at least 4 points), and the "line fit formula" (y=a+bx) is obtained.

3. Calculation of antigen amounts of test samples

Values for a and b are given by the line-fit formula, and y ($\Delta$OD) is known. The remaining unknown value, x, representing the units/mL antigen, can then be calculated, and corrected by the sample dilution to obtain the antigen concentration of the undiluted sample. The reported antigen concentration is that obtained with the least diluted sample providing a $\Delta$OD value within the linear portion of the standard curve.

What is claimed is:

1. A process for preparing a live attenuated thermostable varicella zoster virus (tVZV) which comprises:

a) heating a lyophilized or liquid preparation of live attenuated VZV under highly inactivating conditions; and b) selecting by culturing residual live attenuated VZV.

2. The live attenuated tVZV obtained according to the process of claim 1.

3. A thermostable varicella zoster virus having a rate of inactivation equal to about 50% per hour at 35° C. in a liquid medium.

4. A method of using the tVZV of claim 2 to make a VZV vaccine which comprises combining the tVZV with a pharmaceutically acceptable carrier and providing sufficient tVZV such that a minimum of about 1000 plaque forming units of the virus is available on the date of vaccination in the pharmaceutically acceptable carrier.

5. A method of using the tVZV of claim 3 to make a VZV vaccine which comprises combining the tVZV with a pharmaceutically acceptable carrier and providing sufficient tVZV such that a minimum of about 1000 plaque forming units of the virus is available on the date of vaccination in the pharmaceutically acceptable carrier.

6. A vaccine comprising the tVZV of claim 2.

7. A vaccine comprising the tVZV of claim 3.

8. A thermostable virus selected from the group consisting of ATCC VR2437, ATCC VR2438, and ATCC VR2439.

9. A method of obtaining a tVZV variant which has a rate of inactivation at 35° C. in a liquid medium which is about 38% slower than the live attenuated VZV population from which the tVZV was selected, which comprises:

a) heating a lyophilized or liquid preparation of live attenuated VZV for about 5–19 days at a temperature of 25°–75° C.; and b) selecting by culturing residual live VZV, thus obtaining a tVZV variant which has a rate of inactivation at 35° C. in a liquid medium which is about 38% slower than the VZV population from which the tVZV was selected.

10. A vaccine comprising the tVZV obtained according to the method of claim 9.

11. A multivalent vaccine comprising the tVZV obtained according to the method of claim 9.

12. The method of claim 1 wherein the selected virus is cultured through between one and six cell culture passages.

13. A method for producing a more thermostable VZV (tVZV) than is available in a given live attenuated VZV isolate which comprises:

a) heating a lyophilized or liquid preparation of live attenuated VZV for about 5–19 days at a temperature of 25°–75° C.; and b) selecting by culturing residual live VZV, thus producing a more thermostable VZV (tVZV) than is available in the given live attenuated VZV isolate.

* * * * *